United States Patent [19]

Dubicki et al.

[11] 4,258,191

[45] Mar. 24, 1981

[54] MULTI-STEP PROCESS FOR THE PRODUCTION OF METHANESULFON-M-ANISIDIDE, 4'-(9-ACRIDINYLAMINO)-

[75] Inventors: Henryk Dubicki, Lancaster; Jack L. Parsons, East Aurora; Fred W. Starks, Kenmore, all of N.Y.

[73] Assignee: The United States of America as represented by the Secretary of Health, Education and Welfare, Washington, D.C.

[21] Appl. No.: 25,157

[22] Filed: Mar. 29, 1979

[51] Int. Cl.$^3$ .................... C07D 219/10; A61K 31/47
[52] U.S. Cl. ..................................... 546/106; 424/257
[58] Field of Search ........................................ 546/106

[56] References Cited

U.S. PATENT DOCUMENTS

| | | | |
|---|---|---|---|
| 3,414,587 | 12/1968 | Lehr et al. | 260/335 |
| 3,694,448 | 9/1972 | Ledochowski et al. | 546/106 |

OTHER PUBLICATIONS

Cain, et al., J. Med. Chem., vol. 18(11), pp. 1110–1117 (1975).
Cain, et al., J. Med. Chem., vol. 17(9), pp. 922–930 (1974).
Cain, et al., J. Med. Chem., vol. 19(12), pp. 1409–1416 (1976).
Cain, et al., J. Med. Chem., vol. 20(8), pp. 987–996 (1977).
Albert, "The Acridines", St. Martin's Press, New York (1966), pp. 29–77, 144, 164–165, 264, 265, 518–519.

Primary Examiner—Donald G. Daus
Assistant Examiner—Diana G. Rivers

[57] ABSTRACT

A multi-step method of producing the compound methanesulfon-m-anisidide, 4'-(9-acridinylamino)-, acetate (VII), which may be in free base form and designated NSC 249992, also known as AMSA. This compound is produced by an elegant process from a starting material, 4-butyrylamino-3-methoxy-nitrobenzene, which is later transformed to methanesulfon-m-anisidide, 4'-amino-(IV) and is coupled or joined to 9-chloro-acridine, producing the chloride salt which is later converted to the acetate.

6 Claims, No Drawings

MULTI-STEP PROCESS FOR THE PRODUCTION OF METHANESULFON-M-ANISIDIDE, 4'-(9-ACRIDINYLAMINO)-

The invention described herein was made in the course of work under a grant or award from the Department of Health, Education, and Welfare.

This invention relates to a multi-step process with a reaction sequence as follows:

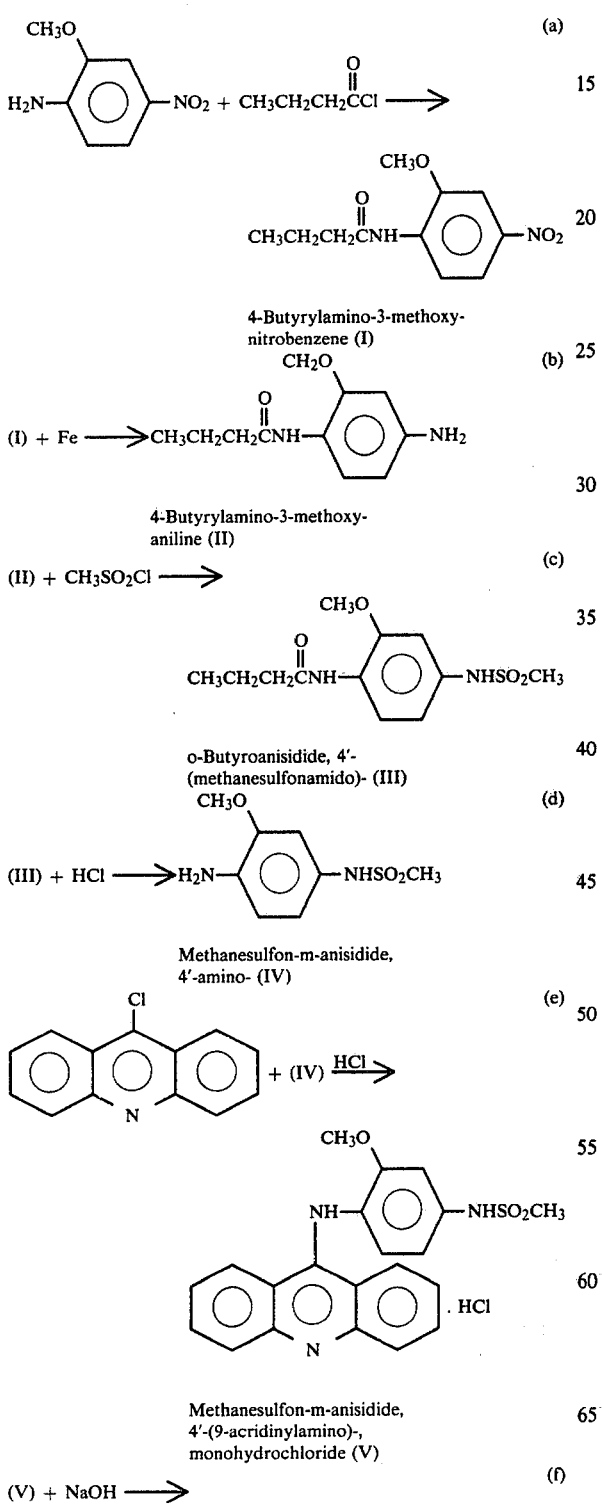

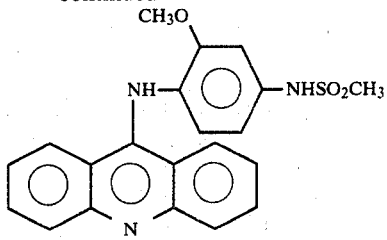

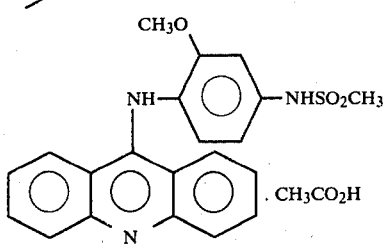

characterized by improvements consisting of (a) the isolation of 4-butyrylamino-3-methoxy nitro benzene (I) by precipitation in water, then purification by washing in water, 2% aqueous HCl, and ethanol; (b) the purification of 4-butyrylamino-3-methoxyaniline (II) by dissolving in methylene chloride, clarifying by filtration, and then proceeding directly to the next step (c); (c) the utilization of methylene chloride as a solvent and using a minimum amount of pyridine as an acid acceptor; (d) the precipitation isolation of methanesulfon-m-anisidide, 4'-amino-(IV) as the hydrochloride salt which, when released with ammonium hydroxide in water, gives an analytically pure product; (e) condensing 9-chloro-acridine with the amine at 55°–60° using methylene chloride/chloroform as both reaction cosolvents and also as a wash for the product, methanesulfon-m-anisidide, 4'-(9-acridinylamino)-, monohydrochloride (V); and (f) neutralizing the hydrochloride in DMAC with aqueous sodium hydroxide at about 40°–55° C. to produce a filterable precipitate, said precipitate being recrystallized in DMF/water at 70°–80° C. to produce an increasedly filterable precipitate (VI).

PRIOR ART STATEMENT

In the literature article by Cain et al, J. Med. Chem., 18(11):1110–1117 (1975), it is pointed out that a 3'-methoxy function markedly increased (2–8 fold) potency with a variety of acceptable acridine ring substituents. The present multi-step process is an improvement over various features recited in this Cain et al article, which reports the structure antileukemic activity against L1210 sulfonanilide ring substituted varieties of 4'-(acridin-9-ylamino)methanesulfonanilides.

Related compounds such as the 9-chloroacridines and 9-aminoacridines are recited in the prior art in a monograph entitled The Acridines by Adrien Albert, 1966, which shows at page 519 a previous testing of acridines in malignancy. Page 519 recites, The Compound "3-chloro-8-methoxy-9-(4-dimethylaminobutylamino)- acridine active against Crocker's sarcoma (Sa 180) in mice."

The patent prior art is as follows:
U.S. Pat. No. 3,414,587 Lehr et al
U.S. Pat. No. 3,694,448 Ledochowski et al As to the general hierarchy and background of the present compound, in Albert's book above, Chapter 2 describes the preparation and uses of 9-chloroacridines by ring closure of diphenylamine-2-carboxylic acids; and Chapter 3, beginning at page 56, describes the preparation of diphenylamine-2-carboxylic acids

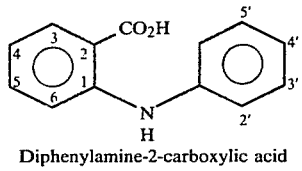

Diphenylamine-2-carboxylic acid

At page 144 of the Albert book there are general hints on the preparation and uses of 9-chloroacridines and at page 164 the same treatment is given for aminoacridines. Page 264 gives a structural formula of a closely related compound which additionally contains a 1-nitro substituent.

The National Cancer Institute has given the designation NSC 249992 to the compound, methanesulfon-m-anisidide, 4'-(9-acridinylamino)-(VI), the free base, and this designation includes the acetate, (VII). A previous designation as to the chloride salt (V) was NSC-141549.

The purpose of this invention is to provide a modus for recounting the production of quantities of the compound in preparation for clinical trial for antitumor antileukemic effect and to produce quantities for clinical studies in multiple clinical sites.

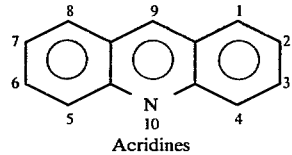

Acridines

ADVANTAGES OVER THE PRIOR ART

Step (a). Novel isolation of the product by precipitation in water avoided laborious spin-evaporation of pyridine and trituration with large volumes of water. A crystallization from large volumes of ethanol (20 ml/g) was avoided by purifying the product through a washing process (water, 2% aqueous hydrochloric acid, then ethanol).

Step (b). The optimization of reaction variables enabled the solvent volume to be reduced from 8 l/kg to 4 l/kg and the quantity of iron to be reduced from 9 equivalents to 2.95 equivalents. A novel approach was made in purification by dissolving the crude residue in methylene chloride, clarifying by filtration, then using directly in the next step. The use of a regulated chemical, benzene, was thus avoided.

Step (c). Methylene chloride was used as a novel solvent for this reaction. Pyridine was utilized only as the acid acceptor instead of the solvent, thus reducing its usage from 15 l. to 0.5 l. per kg. Crystallization of the product was eliminated, thus saving additional volumes of ethanol.

Step (d). The precipitation and isolation of the product as a hydrochloride salt was a key innovation in the purification of compound (IV). Subsequent salt release with ammonium hydroxide in water gave analytically pure product.

Step (e). The original process for condensation of 9-chloroacridine and the requisite amine was unsuitable for large scale work due to the solvent choice, temperature of the reaction, and the hydrochloride obtained was very difficult to filter and purify due to by-product formation of acridone. A mixture of methanol and chloroform was substituted. The temperature of the reaction was held at 55°-60°. The addition of 9-chloroacridine, portion-wise, reduced almost to negligible amounts the production of acridone and other side-products. The hydrochloride precipitated from the reaction mixture in highly crystalline form and high purity, and required no further purification beyond washing with methanol-chloroform to proceed to the next step.

Step (f). The release of the free base was accomplished by neutralizing a suspension of the hydrochloride in DMAC with aqueous sodium hydroxide at 40°-55° to ensure a filterable precipitate. The free base was purified by recrystallization from DMF-water at temperatures of 70°-80°, again to ensure a crystalline material. This also obviated the use of huge volumes of ethanol and water.

The described innovations have led to the production of AMSA [methanesulfon-m-anisidide, 4'-(9-acridinylamino)-, acetate] in multi-kilogram quantities. Table I describes the status of each step. Included in the definition of AMSA is the free base, (VI), ante.

TABLE I

| Step | Scale | Yield |
|---|---|---|
| a | 6 kg (Ia) (22 l. reactor) | 8.1 kg (I) 96% |
| b | 16 kg (I) (50 gal. reactor) | Not isolated |
| c | Material from Step b (100 gal. reactor) | 13.6 kg (III) 71% |
| d | 12.9 kg (III) (50 gal. reactor) | 9.9 kg (IV) 88% |
| E | 8.7 kg (IV 8.0 kg 9-chloroacridine (100 gal. reactor) | 15.5 kg (V) 96% |
| f | 16.1 kg (V) (55 gal. reactor) | 11.0 kg (VI) 75% |

The yields described represent an overall 43% yield for the six-step reaction sequence.

EXAMPLE 1

Production of 4-Butyrylamino-3 -methoxynitrobenzene (I)

A 22-liter reactor equipped with an overhead stirrer, thermometer, dropping funnel, and cooling bath was charged with 4-nitro-o-anisidine (6000 g; 35.70 moles) and dry pyridine (9.0 l.). To the stirred solution was added n-butyryl chloride (4010 g; 37.50 moles) dropwise, during 6 hours. The temperature of the reaction mixture was maintained between 30° and 40° during the addition. The suspension was heated at 100° for 0.5 hour then stored at room temperature for 18 hours. The mixture was blended into ice water (60.0 l.), and the precipitated solid was collected, then washed in succession by resuspension with water (2×18.0 l.), 2% aqueous hydrochloric acid (18.0 l.), water (18.0 l.), and ethanol (3A) (12.0 l.). The ethanol (3A) suspension was cooled to 8°, then the solid was collected and dried to constant weight in vacuo to give 8140 g (96%) of product; m.p., 104°-106°.

EXAMPLE 2

Production of 4-Butyrylamino-3-methoxyaniline (II)

The preparation of this compound was carried out in a 50-gallon Pfaudler reactor. The reactor was purged with nitrogen to a measured oxygen depletion of less than 1% during the entire course of the reaction, including charging and discharging.

A mixture of 4-butyrylamino-3-methoxynitrobenzene (I) (12.5 kg; 52.46 moles), 60% aqueous ethanol (3A) (51.5 l.), acetic acid (4.15 l.), and concentrated hydrochloric acid (140 ml) was prepared in the reactor. The mixture was heated to gentle reflux, then iron (9.50 kg; 170 moles), 40 mesh) was added portionwise, during 9.5 hours. After each iron addition, the reaction mixture was stirred until the exotherm subsided, as determined by measuring the reflux rate. This portionwise addition is described in Table II below.

TABLE II

| Quantity of Iron Added (g) | Time | Quantity of Iron Added (g) | Time |
| --- | --- | --- | --- |
| 100 | Initial | 400 | 4.42 hours |
| 100 | 23 minutes | 400 | 4.67 hours |
| 100 | 42 minutes | 700 | 5.00 hours |
| 100 | 70 minutes | 700 | 5.25 hours |
| 200 | 1.75 hours | 700 | 5.58 hours |
| 200 | 2.00 hours | 700 | 5.83 hours |
| 200 | 2.30 hours | 700 | 6.08 hours |
| 200 | 2.58 hours | 700 | 6.42 hours |
| 200 | 3.00 hours | 700 | 6.67 hours |
| 400 | 3,42 hours | 700 | 6.92 hours |
| 400 | 3.83 hours | 200 | 8.66 hours |
| 400 | 4.08 hours | 300 | 9.46 hours |
| Totall 9500 (g) | | | |

The reaction mixture was refluxed an additional 30 minutes, cooled to room temperature, stored for 12 hours, then calcium carbonate (7.5 kg) was added. The stirred reaction mixture was refluxed for 1.5 hours, then Celite (2 kg) was added. After an additional 1.5 hours of stirring, insolubles were removed from the hot suspension by filtration through Celite. The filter cake was washed with hot (60°), 80% aqueous ethanol (3A) (4×7.0 l.) then room temperature ethanol (3×4.0 l.) The combined filtrates and washings were concentrated in vacuo to a residue which was dissolved in methylene chloride (152 l.) Insolubles were removed by filtration through a Celite pad, then sodium sulfate was added. The mixture was stored for 18 hours, clarified by filtration, then the solution was used immediately in the next reaction.

EXAMPLE 3

Production of o-Butyroanisidide, 4'-(methanesulfonamido)-(III)

To a 50-gallon Pfaudler was added a solution of 4-butyrylamino-3-methoxyaniline (II) (7364 g; 35.36 moles) in methylene chloride (112 l.) and dry pyridine (3.58 l.) The stirred solution was cooled to 4° by circulating brine through the reactor jacket. The temperature was maintained between 2° and 4° while methanesulfonyl chloride (3.44 l.) was added in a thin stream during 5 hours. Cooling was terminated, and the solution was stirred an additional 0.75 hour then stored at room temperature for 15 hours. The solution was concentrated in vacuo to an oil which was blended into cold (10°) water (112 l.) The resulting solid was collected, then washed with water (3×6.0 l.) The material was dissolved in 0.5 N aqueous sodium hydroxide (112 l.), decolorized (charcoal), then filtered through a Celite pad. The product was precipitated from the filtrate by the addition of glacial acetic acid (7.7 l.) which was added in a thin stream during 2 hours. The solid was collected, washed with water (30 l.) until the washings were neutral, then dried to constant weight in vacuo to give 7480 g. (74%) of product. This material was dissolved in a 0.5 N sodium hydroxide solution (82.5 l.), decolorized (charcoal), then filtered through a Celite pad. The product was precipitated from the filtrate by the addition of glacial acetic acid (5.68 l.) which was added in a thin stream during 2 hours. The solid was collected, washed with water (22 l.) until the washings were neutral, then dried to constant weight in vacuo to give 6824 g (67%) of purified product; m.p., 102°-103°.

EXAMPLE 4

Production of Methanesulfon-m-anisidide, 4'-amino-(IV)

To a 50-gallon Pfaudler, purged with nitrogen to a measured oxygen depletion of less than 2%, was added o-butyroanisidide, 4'-(methanesulfonamido)—(III) (8000 g; 27.94 moles), ethanol (3A) (27.2 l.), concentrated hydrochloric acid (9.1 l.), and water (18.1 l.) The stirred mixture was refluxed for 8 hours then cooled to room temperature. The precipitated solid was collected on a filter, washed with ethanol (3A) (3×3.8 l.), then air-dried. The combined filtrate and washings were concentrated in vacuo to yield additional material. The combined solids and water (130 l.) were added to the 50-gallon Pfaudler, then the stirred mixture was heated to 90° under a nitrogen atmosphere. The resulting solution was adjusted to pH 12 by the addition of ammonium hydroxide (6.8 l.), then sodium dithionite (180 g) was added. The solution was heated to 95°, then clarified by filtration. The hot filtrate was transferred to a 55-gallon, stainless steel drum under a nitrogen atmosphere, stored at room temperature for 15 hours, then cooled to 13°. The precipitated solid was collected, washed with cold (5°) water (3×4.0 l.), then dried in vacuo (50°) to constant weight to give 4919 g (81%) of purified product; m.p., 145°-146°.

EXAMPLE 5

Production of Methanesulfon-m-anisidide, 4'-(9-acridinylamino)-, monohydrochloride (V)

To a 100-gallon Pfaudler, purged with nitrogen to a measured oxygen depletion of less than 2%, was added methanesulfon-m-anisidide, 4'-amino-(IV) (8709 g; 40.27 moles), methanol (114 l.), and concentrated hydrochloric acid (589 ml). The stirred mixture was heated to 60°, then a solution of 9-chloroacridine (8004 g; 37.46 moles) in chloroform (68.4 l.) was added in a thin stream during 2.25 hours. The mixture was refluxed for 3 hours, cooled to room temperature, then stored for 15 hours under a nitrogen atmosphere. The solid was collected, washed with methanol-chloroform (1:1) (76 l.), then dried to constant weight in vacuo (65°) to give 16100 g (100%) of product; m.p. 284°-288° (d).

EXAMPLE 6

Production of Methanesulfon-m-anisidide, 4'-(9 acridinyl-amino)-(VI)

To a stirred suspension of methanesulfon-m-anisidide, 4'-(9-acridinylamino)-, monohydrochloride (V) (16100 g; 37.5 moles) in N,N-dimethylacetamide (25.0 l.) was added a solution of sodium hydroxide (1610 g; 40.25 moles) in water (400 l.) during 1.5 hours. The reaction mixture was diluted with water (80 l.), stirred at 40°-50° for 4 hours, then stored for 16 hours at room temperature. The product was collected on a filter, then washed with deionized water (20.0 l.) until the washings were neutral. The free base was dissolved in hot (70°-80°) N,N-dimethylformamide (51 l.), then water (24 l.) was added to the stirred solution until precipitation began. The mixture was stored for 15 hours at room temperature, then cooled to 10°. The precipitated solid was collected, washed with ethanol (4×4.0 l.), then dried in vacuo (40°) to give 11025 g (75%) of purified product; m.p., 230°-231°.

EXAMPLE 7

Production of Methanesulfon-m-anisidide, 4'-(9-acridinylamino)-, acetate (VII)

To a stirred suspension of methanesulfon-m-anisidide, 4'-(9-acridinylamino)-(VI) (5473 g; 13.91 moles) and deionized water (44.58 l.) was added glacial acetic acid (2.476 l.) in a thin stream during 1 hour. The mixture was stirred at room temperature for 3 hours, heated to 75°, then cooled to room temperature during 16 hours. The product was collected on a filter, washed in succession with deionized water (3×6.0 l.) and ethanol (4×4.0 l.), then dried to constant weight in vacuo to give 5678.4 g. (90%) of analytically pure product; m.p., 170° (decomposes to free base).

Anal.

Calc'd. for $C_{23}H_{23}N_3O_5S$

|       | C     | H    | N    | O     | S    |
|-------|-------|------|------|-------|------|
|       | 60.91 | 5.11 | 9.27 | 17.64 | 7.07 |
| Found | 60.88 | 5.18 | 9.29 | 17.61 | 7.06 |

Spectral Data

Infrared (Nujol)

Major bands: 3120, 3040, 2930, 2860, 2730, 1890, 1650, 1590, 1570, 1530, 1510, 1460, 1420, 1405, 1380, 1335, 1265, 1150, 1135, 980, 750 cm$^{-1}$ Ultraviolet (Methanol)

$\lambda_{max}$ 210 nm (50,030); $\lambda_{shoulder}$ 227 nm (30,460);
$\lambda_{max}$ 248 nm (57,950); $\lambda_{shoulder}$ 264 nm (33,380);
$\lambda_{max}$ 412 nm (9,270); $\lambda_{shoulder}$ 444 nm (5,440)

Nuclear Magnetic Resonance (DMSO—d$_6$)

δ7.80-6.40 (m, aromatic H and —NH); 3.50 (s, 3, —SO$_2$C$\underline{H}_3$); 2.90 (s, 3, —OC$\underline{H}_3$); 2.45 (m, DMSO); 1.90 (s, 3, -C$\underline{H}_3$COOH)

Chromatography

Thin Layer Chromatography (Silica Gel, Quanta/-Gram Q6F Glass Plates

| Solvent System | R$_f$Value |
|---|---|
| Isopropanol-ammonium hydroxide-water (7:1:2) | 0.92 |
| n-Butanol-acetic acid-water (7:2:1) | 0.80 |
| Methylene chloride-ethanol (3:2) | 0.83 |

Detection: Ultraviolet light
Quantity Spotted: 50 μg

Results: The compound moved as one spot in each solvent system.

We claim:

1. A process for the production of methanesulfon-m-anisidide, 4'-(9-acridinylamino)-, acetate (NSC 249992) consisting essentially of (a) the isolation of I

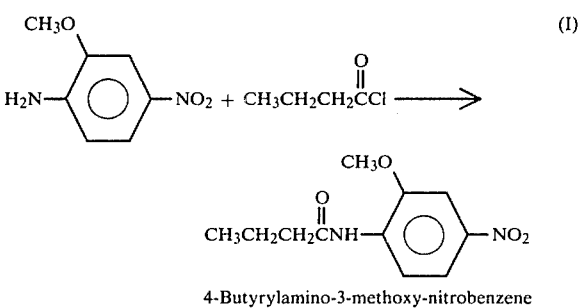

4-Butyrylamino-3-methoxy-nitrobenzene by precipitation in water, then purification by washing in water, 2% aqueous HCl, and ethanol;

(b) the purification of II

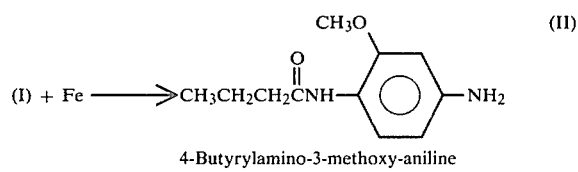

4-Butyrylamino-3-methoxy-aniline by dissolving in methylene chloride, clarifying by filtration, and then proceeding directly to step (c);

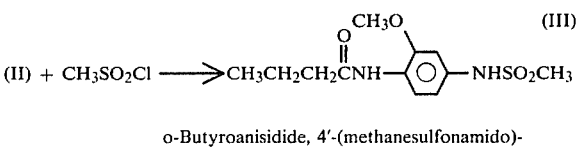

o-Butyroanisidide, 4'-(methanesulfonamido)- the utilization of methylene chloride as a solvent and using a minimum amount of pyridine as an acid acceptor;

(d) the precipitation isolation of IV

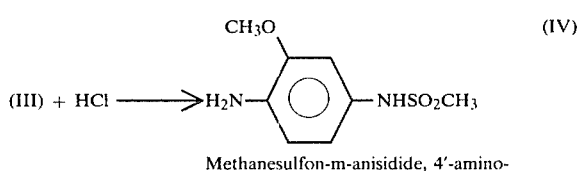

Methanesulfon-m-anisidide, 4'-aminoas the hydrochloride salt which, when released with ammonium hydroxide in water, gives an analytically pure product;

(e) condensing 9-chloro-acridine with the amine at 55°-60° using methylene chloride/chloroform as both reaction cosolvents and also as a wash for the product V

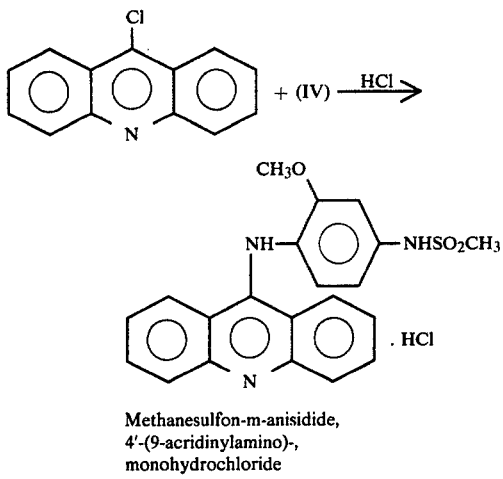

Methanesulfon-m-anisidide,
4'-(9-acridinylamino)-,
monohydrochloride (f) neutralizing the hydrochloride in DMAC with aqueous sodium hydroxide at about 40°–55° C. to produce a filterable precipitate, said precipitate being recrystallized in DMF/water at 70°–80° C. to produce an increasedly filterable precipitate VI

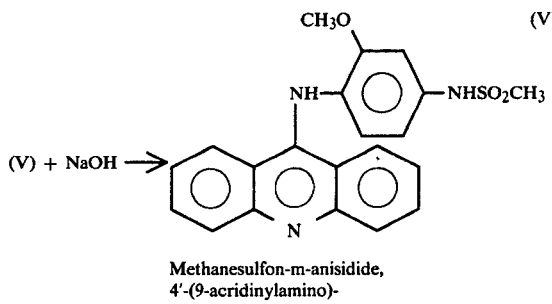

Methanesulfon-m-anisidide,
4'-(9-acridinylamino)-

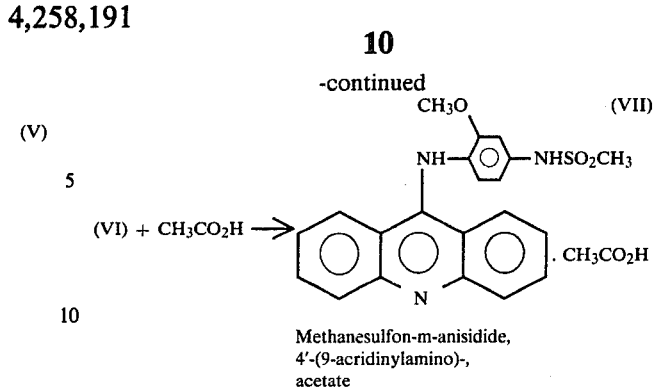

Methanesulfon-m-anisidide,
4'-(9-acridinylamino)-,
acetate

2. In the process according to claim 1 step (c), consists of the increment invention which comprises utilizing methylene chloride as a solvent and using a minimum amount of pyridine as an acid acceptor.

3. In the process according to claim 1 and in step (d), the improvement which consists of the precipitation isolation of methanesulfon-m-anisidide, 4'-amino-(IV) as the hydrochloride salt which, when released with ammonium hydroxide in water, gives an analytically pure product.

4. In the process according to claim 1 and in step (e), the improvement wherein 9-chloro-acridine is condensed with the amine at 55°–60° using methylene chloride/chloroform as both reaction cosolvents and also as a wash for the product, methanesulfon-m-anisidide, 4'-(9-acridinylamino)-, monohydrochloride (V).

5. In the process according to claim 1 and in step (f), the improvement which comprises neutralizing the hydrochloride in DMAC with aqueous sodium hydroxide at about 45°–50° C. to produce a filterable precipitate, said precipitate being recrystallized in DMF/water at 70°–80° C. to produce an increasedly filterable precipitate (VI).

6. The process according to claim 5 wherein VI is reacted under mild heat conditions with acetic acid to produce methanesulfon-m-anisidide, 4'-(9-acridinylamino)-, acetate (VII).

* * * * *